United States Patent [19]

Weber et al.

[11] Patent Number: 5,637,786
[45] Date of Patent: Jun. 10, 1997

[54] SERIES PARALLEL HEATED OXYGEN SENSOR HEATER CONTROL

[75] Inventors: David C. Weber, Toledo, Ohio; Alan M. Rooke, Dearborn, Mich.

[73] Assignee: Ford Motor Company, Dearborn, Mich.

[21] Appl. No.: 498,193

[22] Filed: Jul. 5, 1995

[51] Int. Cl.$^6$ ...................................................... H05B 1/02
[52] U.S. Cl. ................................ 73/23.32; 123/697
[58] Field of Search ................................ 73/23.31, 23.32, 73/116, 117.2, 117.3, 118.1; 123/697

[56] References Cited

U.S. PATENT DOCUMENTS

| | | |
|---|---|---|
| 4,033,170 | 7/1977 | Kawamura et al. |
| 4,170,967 | 10/1979 | Wessel et al. ........................ 123/697 |
| 4,332,225 | 6/1982 | Cox et al. ............................ 123/697 |
| 4,348,583 | 9/1982 | Bube et al. ........................ 123/179.21 |
| 4,504,732 | 3/1985 | Bube et al. ........................ 123/179.21 |
| 4,561,402 | 12/1985 | Nakano et al. ...................... 73/23.32 |
| 4,580,539 | 4/1986 | Kitahara ............................... 123/686 |
| 4,611,562 | 9/1986 | Nakano et al. ...................... 73/23.32 |
| 4,655,182 | 4/1987 | Nakano et al. |
| 4,803,866 | 2/1989 | Miki et al. ........................... 73/23.32 |
| 4,938,196 | 7/1990 | Hoshi et al. ......................... 73/23.32 |
| 4,993,392 | 2/1991 | Tanaka et al. ....................... 73/23.32 |
| 5,101,625 | 4/1992 | Sugino et al. .......................... 60/276 |
| 5,148,795 | 9/1992 | Nagai et al. ......................... 123/697 |
| 5,279,145 | 1/1994 | Suzuki ................................. 73/23.32 |

*Primary Examiner*—Richard Chilcot
*Assistant Examiner*—Eric S. McCall
*Attorney, Agent, or Firm*—Peter Abolins

[57] ABSTRACT

This invention teaches a series parallel heated oxygen sensor control wherein a parallel portion is used to apply heat to the oxygen sensor during warm-up and a series portion is used to apply heat to the oxygen sensor afterwards so that about one quarter of the amount of power is applied after warm-up.

2 Claims, 1 Drawing Sheet

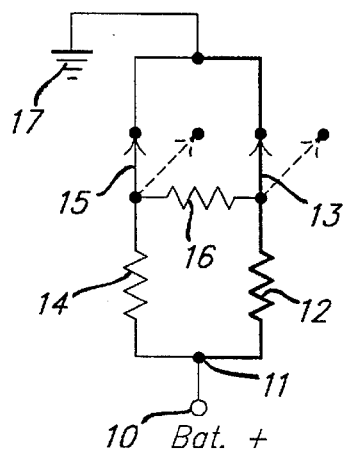
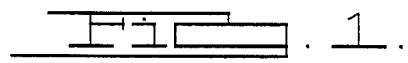
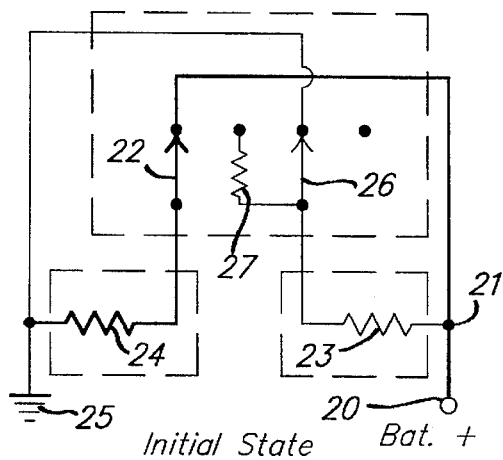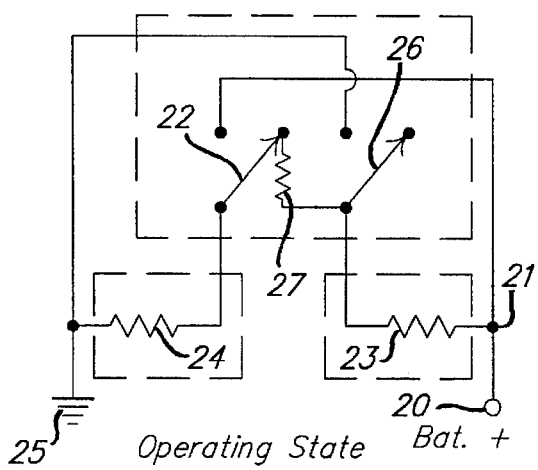
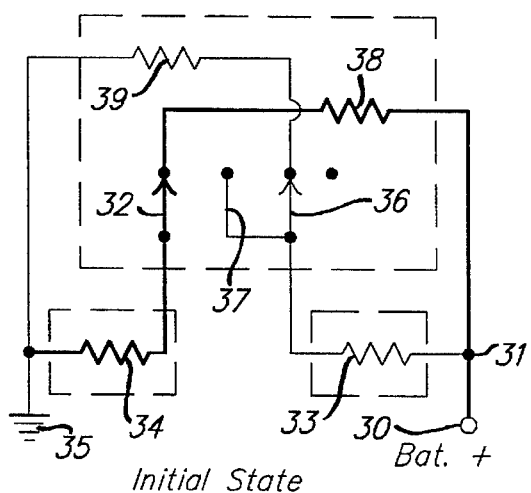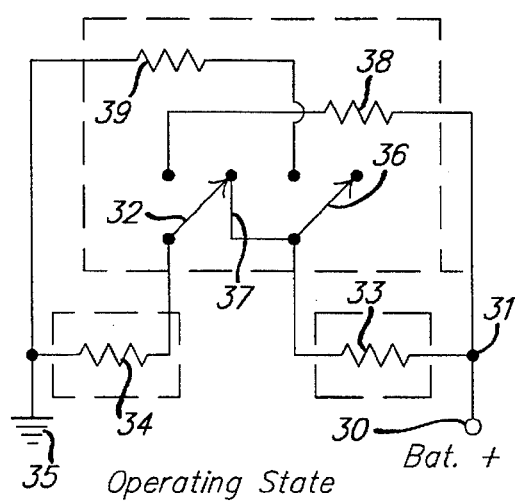
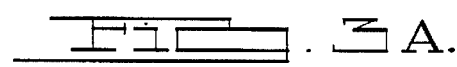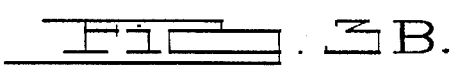

SERIES PARALLEL HEATED OXYGEN SENSOR HEATER CONTROL

BACKGROUND OF THE INVENTION

1. Field of the Invention

This invention relates to electronic engine controls for an internal combustion engine.

2. Prior Art

It is known to use heated oxygen sensors in the exhaust gas from an internal combustion engine to produce a signal indicative of the amount of oxygen in the exhaust gas. An exhaust gas oxygen sensor operates with an improved efficiency within a certain temperature range. It is desirable to get the temperature of the exhaust gas oxygen sensor to be within this temperature range quickly.

Referring to FIG. 1, during startup of an engine, in accordance with a known circuit, approximately 14 volts of electricity from a battery 10 flows to a node 11 where the current is split between two paths. One path leads half of the total current through a HO2S 12 to a switch 13 which is typically closed during engine startup and also running mode as needed. From switch 13 the flow concludes at a battery ground 17. The other path leads the other half of the total current through a HO2S 14 to a switch 15 which also remains closed during engine startup and operating mode. The flow ends at battery ground 17. A bridge resistor 16 is used to periodically check the current through each path by opening one of the switches. In operation, the current through the HO2S's is the same during start-up as during normal operation. It would be desirable to get a faster initial warm up. These are some of the problems this invention overcomes.

SUMMARY OF THE INVENTION

This invention provides a structure to allow a faster light-off time of a heated oxygen sensor and thus improve operation of an air fuel control system for an internal combustion engine.

Advantages of this invention include allowing powering of the heated exhaust gas oxygen sensor at four times the normal operating power for short time periods and not requiring any additional pins or connections to an associated electronic engine control module.

BRIEF DESCRIPTION OF THE INVENTION

FIG. 1 is a prior art schematic diagram of a heated exhaust gas oxygen sensor controller circuit in an engine startup position;

FIG. 2A is a schematic diagram of a heated exhaust gas oxygen sensor controller circuit in an engine startup position in accordance with an embodiment of this invention;

FIG. 2B is a schematic diagram of a heated exhaust gas oxygen sensor controller circuit in an engine steady state running position in accordance with an embodiment of this invention;

FIG. 3A is a schematic diagram of an alternate heated exhaust gas oxygen sensor controller circuit in an engine startup position in accordance with an embodiment of this invention; and FIG. 3B is a schematic diagram of an alternate heated exhaust gas oxygen sensor controller circuit in an engine steady state running position in accordance with an embodiment of this invention.

DETAILED DESCRIPTION OF THE INVENTION

In accordance with this invention heated oxygen sensors (HO2S's) are powered at four times the power using a parallel circuit for warm-up. Then, the HO2S's are powered at normal operating power with a series circuit.

Referring to FIG. 2A, during startup of the engine, approximately 14 volts is applied from a battery 20 to a node 21, through a switch 22, through a HO2S 24, and to a battery ground 25. The other path is from battery 20 to node 21, through a HO2S 23, through a switch 26, and to battery ground 25. Since power $=V^2/R$, where V is the battery voltage and R is the resistance of the exhaust gas oxygen sensor heater, the parallel circuit provides four times the amount of power that the same circuit would if it were serial.

FIG. 2B is the same circuit as FIG. 2A but with switches 22 and 26 set to serial mode. After HO2S 23 and HO2S 24 reach operating temperatures, switches 22 and 26 open creating a serial path. With the switches open, the battery voltage is split between HO2S sensors 23 and The path runs from battery 20 through HO2S 23, through a sense resistor 27, through switch 22, through HO2S 24, and ends at battery ground 25.

FIG. 3A is an alternative circuit to FIG. 2A. During start-up of the engine, voltage from a battery 30 is applied to two parallel legs. For one leg, current flows from battery 30 to a node 31, through a HO2S 33, through a switch 36, through a sense resistor 39, and to a battery ground 35. The other leg has current flow from battery 30 to node 31, through a sense resister 38, through a switch 32, through HO2S 34 and to a battery ground 35.

FIG. 3B is the same circuit as FIG. 3A but with switches 32 and 36 set to serial mode. After HO2S 33 and HO2S 34 reach operating temperatures, switches 32 and 36 open creating a serial path. The path runs from battery 30 to node 31, through HO2S 33, through a shunt 37, through HO2S 34, and to battery ground 35.

The advantage of the circuit shown in FIGS. 3A and 3B, as opposed to the circuits shown in FIGS. 2A and 2B, is that the current can be sensed for the individual sensor heaters. This is more effective for fault isolation. Also, the sensing is only during start-up or for short periods of time during operation mode. This reduces the heat load on the powertrain control module.

Various modification and variations will no doubt occur to those skilled in the arts to which this invention pertains. Such modifications which basically rely on the teachings through which this disclosure has advanced the art are properly considered with the scope of this invention.

We claim:

1. A circuit for applying power to multiple heaters of a heated exhaust gas oxygen sensor including:

a first parallel configuration of multiple heaters;

a serial configuration that reduces the power in a heater to ¼ that of said first parallel configuration; and further including a switching means to change the coupling of the said multiple heaters from the parallel to the serial configuration.

2. A circuit as recited in claim 1 further comprising a sensing resistor in each of the two branches of the first parallel circuit for sensing the amount of current flowing through the heated exhaust gas oxygen sensor.

* * * * *